(12) United States Patent
Nagasaka (10) Patent No.: US 11,321,832 B2
(45) Date of Patent: May 3, 2022

(54) IMAGE ANALYSIS DEVICE

(71) Applicant: Toru Nagasaka, Nagoya (JP)

(72) Inventor: Toru Nagasaka, Nagoya (JP)

(73) Assignee: Toru Nagasaka, Nagoya (JP)

( * ) Notice: Subject to any disclaimer, the term of this patent is extended or adjusted under 35 U.S.C. 154(b) by 98 days.

(21) Appl. No.: 16/757,988

(22) PCT Filed: Oct. 24, 2017

(86) PCT No.: PCT/JP2017/038404
§ 371 (c)(1),
(2) Date: Apr. 21, 2020

(87) PCT Pub. No.: WO2019/082283
PCT Pub. Date: May 2, 2019

(65) Prior Publication Data
US 2020/0342590 A1    Oct. 29, 2020

(51) Int. Cl.
*G06T 7/00* (2017.01)
(52) U.S. Cl.
CPC .. *G06T 7/0012* (2013.01); *G06T 2207/20021* (2013.01); *G06T 2207/20076* (2013.01); *G06T 2207/30024* (2013.01)
(58) Field of Classification Search
CPC ......... G06T 7/0012; G06T 2207/20021; G06T 2207/20076; G06T 2207/30024
See application file for complete search history.

(56) References Cited

U.S. PATENT DOCUMENTS

| | | | |
|---|---|---|---|
| 8,582,860 B2 | 11/2013 | Malon et al. | |
| 8,594,411 B2 | 11/2013 | Yoshihara et al. | |
| 9,760,807 B2 * | 9/2017 | Zhou | G06T 7/0014 |

(Continued)

FOREIGN PATENT DOCUMENTS

| | | |
|---|---|---|
| JP | 2001059842 A | 3/2001 |
| JP | 2004286666 A | 10/2004 |

(Continued)

OTHER PUBLICATIONS

Extended European Search Report for European Patent Application No. 17929925.0 dated Sep. 11, 2020.

(Continued)

*Primary Examiner* — Vu Le
*Assistant Examiner* — Julius Chai
(74) *Attorney, Agent, or Firm* — K&L Gates LLP (57) ABSTRACT

An image analysis device may obtain target image data representing a target image which is an analysis target, specify (m×n) partial images sequentially by scanning the target image data, wherein the (m×n) partial images are constituted of m partial images aligned along a first direction and n partial images aligned along a second direction, generate first probability data by using the (m×n) partial images and the first object data in the memory, and reduce the target image data so as to generate reduced image data. The image analysis device may execute image analysis according to a convolutional neural network by using the reduced image data as K pieces of channel data corresponding to K channels and using the first probability data as one piece of channel data corresponding to one channel, and output a result of the image analysis.

6 Claims, 8 Drawing Sheets

(56) References Cited

U.S. PATENT DOCUMENTS

| | | | |
|---|---|---|---|
| 10,275,688 B2* | 4/2019 | Jiang | G06K 9/6282 |
| 10,870,887 B2* | 12/2020 | Rotthier | C12Q 1/6883 |
| 2011/0206282 A1* | 8/2011 | Aisaka | G06T 11/60 |
| | | | 382/195 |
| 2012/0076417 A1* | 3/2012 | Yoshii | G06K 9/6292 |
| | | | 382/190 |
| 2012/0082365 A1 | 4/2012 | Yoshihara et al. | |
| 2015/0332435 A1* | 11/2015 | Motohashi | G06T 3/4053 |
| | | | 382/171 |
| 2017/0046616 A1* | 2/2017 | Socher | G06K 9/4628 |
| 2018/0365794 A1* | 12/2018 | Lee | G06T 1/20 |

FOREIGN PATENT DOCUMENTS

| | | |
|---|---|---|
| JP | 2004340738 A | 12/2004 |
| JP | 2010281636 A | 12/2010 |
| JP | 2011527056 A | 10/2011 |
| JP | 2015095042 A | 5/2015 |
| WO | 2010003043 A2 | 1/2010 |
| WO | 2019082283 A1 | 5/2019 |

OTHER PUBLICATIONS

Yuezhang Li et al., Object-sensitive Deep Reinforcement Learning, 3rd Global Conference on Artificial Intelligence (GCAI-17), EPiC Series in Computing (Oct. 18, 2017), pp. 20-35, retrieved from https://scholar.google.com/scholar?q=object-sensitive+deep+reinforcement+learning&hl=en&as_sdt=0&as_vis=1&oi=scholart.

International Search Report and Written Opinion for PCT/JP2017/038404 dated Dec. 19, 2017 (English translation).

Kiho, Yosuke et al., Proceedings of the 50th IPSJ Annual Convention(2), Mar. 15, 1995, pp. 215-216.

Kiho, Yosuke et al., IEICE, Technical Report, Mar. 14, 1996, vol. 95, No. 583, pp. 79-84.

Murata, Kenta, Web+DB Press, Nov. 25, 2015, vol. 89, pp. 67-72.

Japanese Office action for corresponding Japanese Patent Application No. 2019-549725, dated Apr. 13, 2021 (translation version).

International Preliminary Report on Patentability for PCT/JP2017/038404 dated Jun. 26, 2018 (English translation).

Japanese Office action for correspondence Japanese Patent Application No. 2019-549725, dated Jan. 19, 2021 (English translation included).

* cited by examiner

-PRIOR ART-

FIG. 3A

-PRIOR ART-

FIG. 3B

-PRIOR ART-

FIG. 3C

-PRIOR ART-

IMAGE ANALYSIS DEVICE

CROSS-REFERENCE TO RELATED APPLICATIONS

This application is a U.S. National Stage Entry under 35 U.S.C. § 371 of International Patent Application No. PCT/JP2017/038404, filed Oct. 24, 2017, entitled IMAGE ANALYSIS DEVICE, the entire disclosure of which is hereby incorporated by reference herein in its entirety and for all purposes.

TECHNICAL FIELD

The description herein discloses an image analysis device configured to execute image analysis according to a convolutional neural network.

BACKGROUND ART

Conventionally, image analysis that uses an image analysis device is known (for example, Japanese Patent Application Publication Nos. 2001-59842, 2010-281636, 2004-286666, and 2011-527056). Especially, Japanese Patent Application Publication No. 2011-527056 executes image analysis according to a convolutional neural network.

SUMMARY OF INVENTION

Technical Problem

In order to execute image analysis promptly, a consideration may be given for example to executing the image analysis by generating reduced image data by reducing target image data of an analysis target and executing the image analysis according to the convolutional neural network using the reduced image data. However, the image analysis using the reduced image data may have degraded analysis accuracy.

The description herein discloses an art that enables to achieve improvement in analysis accuracy of image analysis using reduced image data.

An image analysis device disclosed herein may comprise: a memory configured to store first object data representing a first object; an obtaining unit configured to obtain target image data representing a target image which is an analysis target, wherein the target image data includes (M×N) pixels constituted of M pixels aligned along a first direction and N pixels aligned along a second direction orthogonal to the first direction, the M being an integer of 3 or greater, and the N being an integer of 3 or greater, and wherein each pixel of the (M×N) pixels indicates K values corresponding to K channels, the K being an integer of 1 or greater; a specifying unit configured to specify (m×n) partial images sequentially by scanning the target image data, wherein the (m×n) partial images are constituted of m partial images aligned along the first direction and n partial images aligned along the second direction, the m being an integer of 2 or greater and less than the M, and the n being an integer of 2 or greater and less than the N; a first generating unit configured to generate first probability data by using the (m×n) partial images and the first object data in the memory, wherein the first probability data includes (m×n) pixels constituted of m pixels aligned along the first direction and n pixels aligned along the second direction, and wherein each pixel of the (m×n) pixels included in the first probability data indicates a value related to a probability that one partial image corresponding to the pixel includes the first object; a reducing unit configured to reduce the target image data so as to generate reduced image data, wherein the reduced image data includes (m×n) pixels constituted of m pixels aligned along the first direction and n pixels aligned along the second direction; an analysis unit configured to execute image analysis according to a convolutional neural network by using the reduced image data as K pieces of channel data corresponding to the K channels and using the first probability data as one piece of channel data corresponding to one channel; and an output unit configured to output a result of the image analysis.

According to the above configuration, upon execution of the image analysis according to the convolutional neural network, the image analysis device not only uses the reduced image data as the K pieces of channel data corresponding to the K channels but also uses the first probability data as the one piece of channel data corresponding to the one channel. Due to this, the image analysis device can improve analysis accuracy related to the first object in the image analysis using reduced image data.

The K channels may be three channels of RGB. According to this configuration, the image analysis device can execute the image analysis by using the reduced image data as three pieces of channel data corresponding to the three channels of RGB.

The memory may be further configured to store second object data representing a second object different from the first object. The image analysis device may further comprise: a second generating unit configured to generate second probability data by using the (m×n) partial images and the second object data in the memory, wherein the second probability data includes (m×n) pixels constituted of m pixels aligned along the first direction and n pixels aligned along the second direction, and each pixel of the (m×n) pixels included in the second probability data indicates a value related to a probability that one partial image corresponding to the pixel includes the second object. The analysis unit may execute the image analysis by using the reduced image data as the K pieces of channel data, using the first probability data as the one piece of channel data corresponding to the one channel, and using the second probability data as one piece of channel data corresponding to one channel. According to this configuration, the image analysis device can improve both the analysis accuracy related to the first object and analysis accuracy related to the second object in the image analysis using reduced image data.

The first object may be a predetermined cell. According to this configuration, the image analysis device can improve the analysis accuracy related to the first object being the predetermined cell.

The present technology is also applicable to an image analysis method. A control method, a computer program and a non-transitory computer-readable medium storing the computer program for implementing the above image analysis device are also novel and useful.

Figure 1:
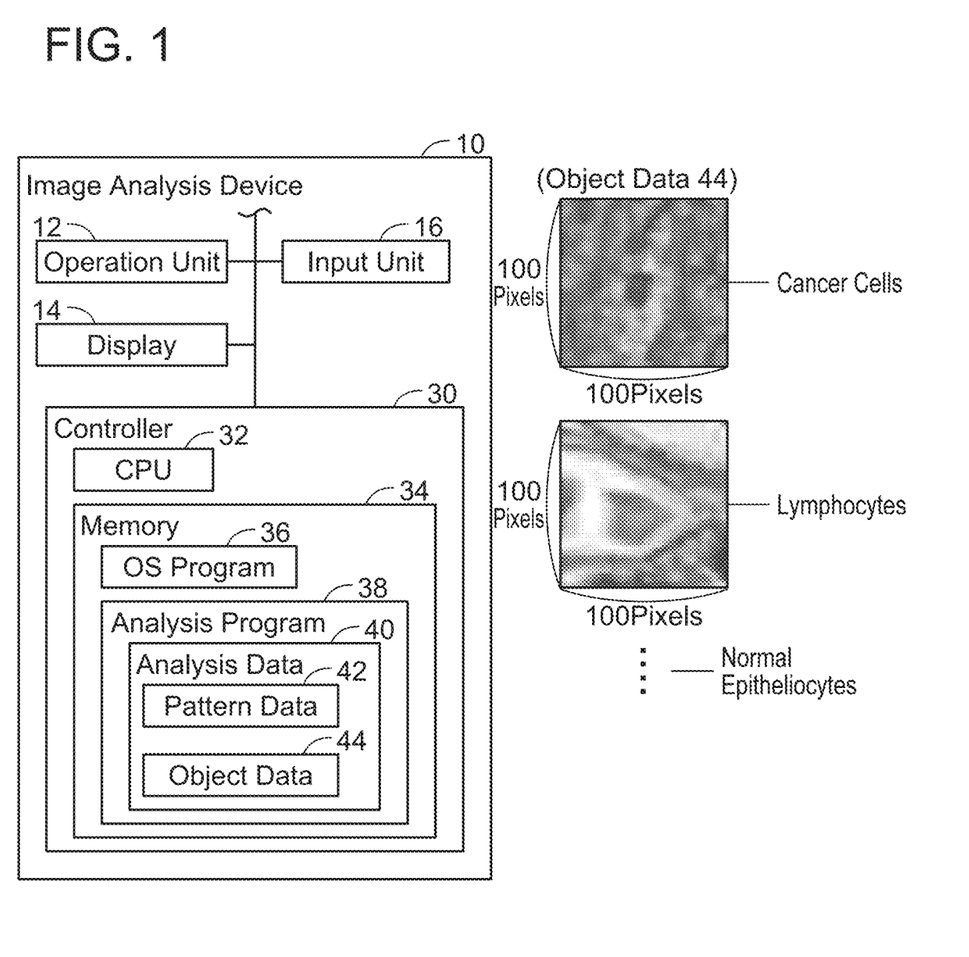
FIG. 1 shows a block diagram of an image analysis device.

(Configuration of Image Analysis Device: FIG. 1)

FIG. 1 shows a configuration of an image analysis device 10 configured to execute image analysis on an image including cell(s). The image analysis device 10 comprises an operation unit 12, a display 14, an input unit 16, and a controller 30. The respective units 12 to 30 are connected to a bus line (reference sign omitted). The operation unit 12 comprises a mouse and a keyboard, for example. A user can provide various instructions to the image analysis device 10 by operating the operation unit 12. The display 14 is a display configured to display various types of information.

The input unit 16 is a device configured to input target image data representing a target image being an analysis target to the image analysis device 10. In the present embodiment, the target image data includes a plurality of cell objects corresponding to a plurality of cells. The input unit 16 may be a communication interface configured to execute wired or wireless communication, or may be a memory interface to which a USB memory or the like is to be inserted. For example, the target image data may be inputted to the image analysis device 10 by the input unit 16 executing wired or wireless communication with a device storing image data captured by a microscope, a Whole Slide Image (virtual slide) captured by a scanner, and the like, as the target image data and receiving the target image data from this device. Further, for example, the target image data may be inputted to the image analysis device 10 by the input unit 16 reading the target image data from a memory storing the target image data.

The controller 30 comprises a CPU 32 and a memory 34. The CPU 32 is configured to execute various processes in accordance with programs 36, 38 stored in the memory 34. The memory 34 stores an OS program 36 for realizing basic operations of the image analysis device 10 and an analysis program 38 for executing image analysis according to a convolutional neural network (hereinbelow termed "CNN (abbreviation of Convolutional Neural Network)"). Here, the image analysis according to the CNN is a concept that encompasses image analysis according to a large-scale network including the CNN as a partial structure thereof (such as GoogLeNet (registered trademark) and Residual Network). For example, the image analysis device 10 may be realized by installing the analysis program 38 on a general-purpose PC or server.

Further, the memory 34 stores analysis data 40 for executing the image analysis according to the analysis program 38. The analysis data 40 may be data provided from a vendor who sells the analysis program 38 or may be data generated by the user of the image analysis device 10. In the former case, the analysis data 40 is stored in the memory 34 upon installation of the analysis program 38. In the latter case, the analysis data 40 is stored in the memory 34 by the user of the image analysis device 10 after the installation of the analysis program 38.

The analysis data 40 includes pattern data 42 and object data 44. The pattern data 42 is data used in a convolutional layer in the image analysis according to the CNN. The object data 44 includes object data representing images including cell objects respectively indicating types of plural cells (such as a cancer cell, a lymphocyte, and a normal epitheliocyte).

Figure 2:
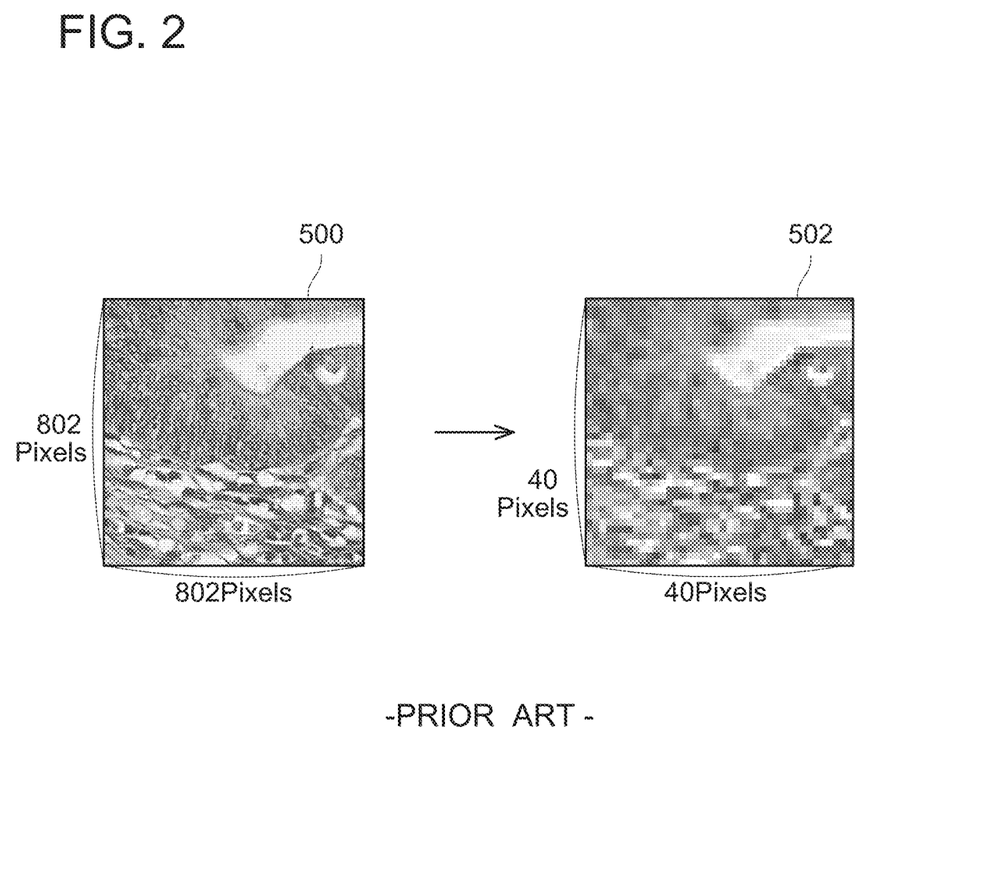
FIG. 2 shows an example of a target image and a reduced image.
Figure 3A:
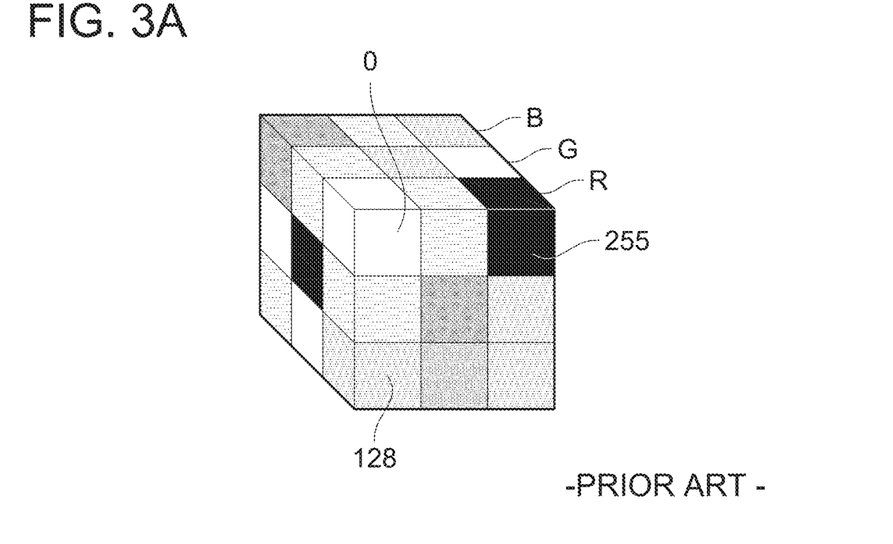
FIGS. 3A to 3C show an explanatory diagram for explaining conventional image analysis.
Figure 3B:
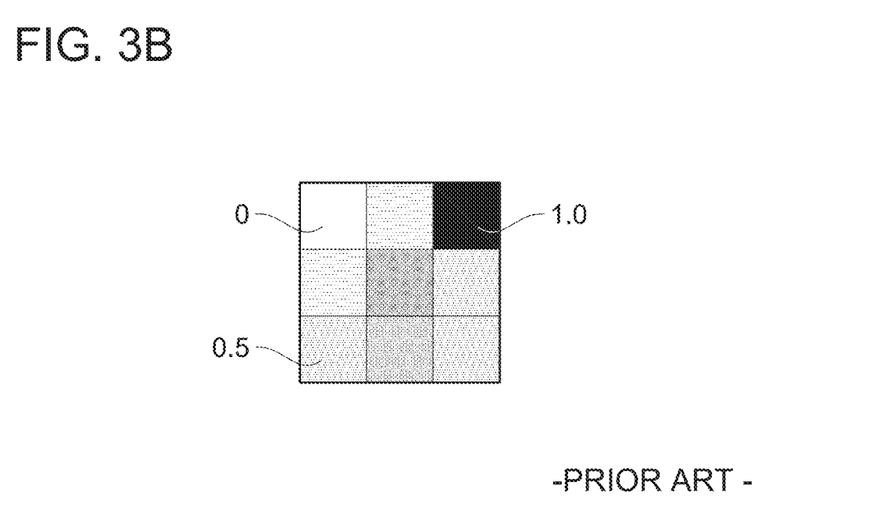
Figure 3C:
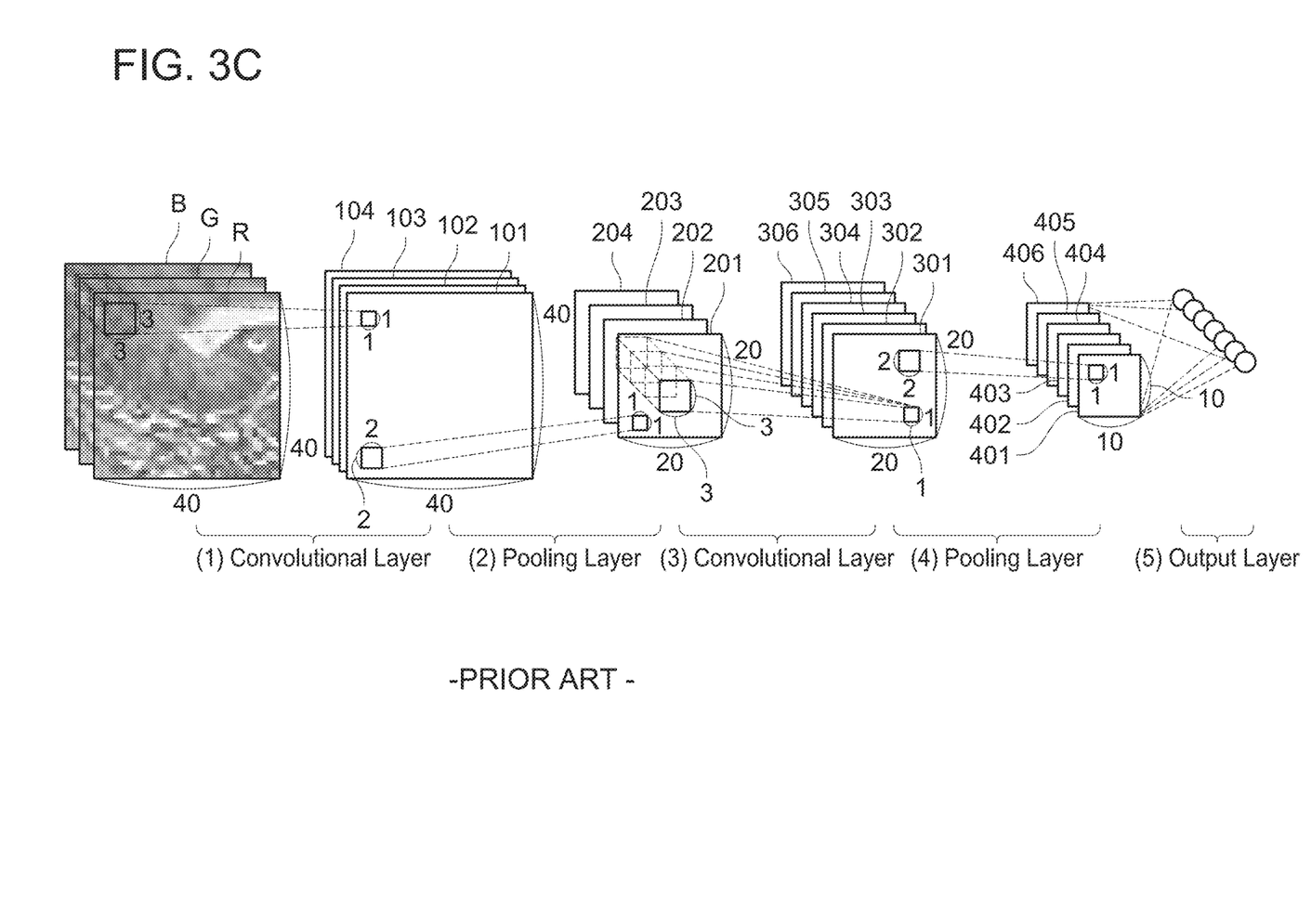

(Conventional Image Analysis: FIGS. 2 and 3)

Next, contents of conventional image analysis will be described with reference to FIGS. 2 and 3. In the conventional image analysis, firstly, an image analysis device obtains target image data. FIG. 2 shows an example of a target image 500 represented by the target image data. The target image data includes (802×802) pixels constituted of 802 pixels aligned along a lateral direction and 802 pixels aligned along a vertical direction. In a variant, target image data may have pixels in numbers different from 802 aligned along the lateral and vertical directions. Further, a number of pixels aligned along the lateral direction and a number of pixels aligned along the vertical direction may be different from each other. Each of the pixels indicates RGB values in a multilevel gradation (such as 256-level gradation). That is, each pixel indicates three values corresponding to three channels being RGB (that is, the RGB values).

Next, the image analysis device reduces the target image data to generate reduced image data. FIG. 2 shows an example of a reduced image 502 represented by the reduced image data. The reduced image data includes (40×40) pixels constituted of 40 pixels aligned along the lateral direction and 40 pixels aligned along the vertical direction. In a variant, pixels in numbers different from 40 may be aligned along the lateral and vertical directions. Further, a number of pixels aligned along the lateral direction and a number of pixels aligned along the vertical direction may be different from each other.

Next, the image analysis device executes the following processes (1) to (5) by using the reduced image data as three pieces of channel data corresponding to the three channels. As shown in FIG. 3(C), (1) the image analysis device firstly executes a convolutional layer process on the reduced image data. Three-layer pattern data included in the pattern data 42 is used in a convolutional layer hereof. FIG. 3(A) shows an example of the three-layer pattern data. The three-layer pattern data may for example be data for detecting features of a cancer cell (such as edge and texture thereof), and includes one layer of data corresponding to R values, one layer of data corresponding to G values, and one layer of data corresponding to B values. Each of the three layers of data includes (3×3) pixels constituted of 3 pixels aligned along the lateral direction and 3 pixels aligned along the vertical direction. That is, the three-layer pattern data is constituted of (3×3×3) pixels. Each pixel indicates a value in the multilevel gradation (such as 256-level gradation). FIG. 3(A) shows values of the respective pixels by darkness of color. The image analysis device specifies the (3×3) pixels included in the reduced image data as a target pixel group, and compares (3×3) R values included in this target pixel group with the (3×3) R values included in the one layer corresponding to the R values in the three-layer pattern data. Similarly, the image analysis device executes comparisons for the G values and the B values as well. Then, the image analysis device uses the comparison results of the RGB to calculate a match rate between the target pixel group and the three-layer pattern data. The match rate is represented by a value in a range of "0" to "1". The image analysis device generates a primary feature map 101 in which respective match rates as specified are described by sequentially specifying target pixel groups from the reduced image data to sequentially specify the match rates thereof. The primary feature map 101 includes (40×40) pixels constituted of 40 pixels aligned along the lateral direction and 40 pixels aligned along the vertical direction, and each pixel indicates the match rate.

Normally, a plurality of pieces of three-layer pattern data is prepared rather than just one piece of three-layer pattern data. For example, a plurality of pieces of three-layer pattern data corresponding to different features (such as edge and texture) of a same cell (such as the cancer cell) may be prepared. Further, for example, a plurality of pieces of three-layer pattern data corresponding to a feature (such as edge or texture) of plural types of cells may be prepared. The image analysis device generates a plurality of primary feature maps 101 to 104 corresponding to the plurality of pieces of three-layer pattern data by executing the convolutional layer process respectively on the plurality of pieces of three-layer pattern data.

(2) The image analysis device executes a pooling layer process on the generated primary feature map 101. Specifically, the image analysis device specifies (2×2) pixels included in the primary feature map 101 as a target pixel group and specifies a largest match rate in the target pixel group (that is, among the four match rates). The image analysis device sequentially specifies largest match rates by sequentially specifying target pixel groups from the primary feature map 101 and generates a reduced primary feature map 201 which describes the respective match rates as specified. The reduced primary feature map 201 includes (20×20) pixels constituted of 20 pixels aligned along the lateral direction and 20 pixels aligned along the vertical direction. The image analysis device generates a plurality of reduced primary feature maps 201 to 204 corresponding to the plurality of primary feature maps 101 to 104 by executing same processes for the other primary feature maps 102 to 104 as well. In a variant, reduced primary feature maps in each of which an average of the four match rates in each of the target pixel groups is described instead of the largest match rate may be generated.

(3) The image analysis device executes a convolutional layer process on the generated reduced primary feature maps. Single-layer pattern data included in the pattern data 42 is used in the convolutional layer hereof. FIG. 3(B) shows an example of the single-layer pattern data. The single-layer pattern data may for example be data representing a feature of the cancer cell and include (3×3) pixels constituted of 3 pixels aligned along the lateral direction and 3 pixels aligned along the vertical direction, and each pixel is represented by a value in the range of "0" to "1". In FIG. 3(B), values of the respective pixels are represented by the darkness of color. The image analysis device specifies (3×3) pixels included in the reduced primary feature map 201 as a target pixel group and compares (3×3) match rates included in this target pixel group with the (3×3) values included in the single-layer pattern data. Then, the image analysis device uses the comparison result to calculate a match rate between the target pixel group and the single-layer pattern data. The image analysis device sequentially calculates match rates by sequentially specifying target pixel groups from the reduced primary feature map to generate an intermediate map in which the calculated respective match rates are described. Further, the image analysis device generates three intermediate maps by executing same processes for the other reduced primary feature maps 202 to 204 as well. Then, the image analysis device combines the generated four intermediate maps to generate a secondary feature map 301. Specifically, in the secondary feature map 301, an average of values of four pixels located at a same position among the four intermediate maps is described. The secondary feature map 301 includes (20×20) pixels constituted of 20 pixels aligned along the lateral direction and 20 pixels aligned along the vertical direction, and each pixel indicates the match rate (that is, a value in the range of "0" to "1").

Normally, a plurality of pieces of single-layer pattern data is prepared. The image analysis device executes the convolutional layer process for each of the plurality of pieces of single-layer pattern data to generate a plurality of secondary feature maps 301 to 306 corresponding to the plurality of pieces of single-layer pattern data.

(4) The image analysis device executes a pooling layer process on the generated secondary feature map 301. The pooling layer process is same as the pooling layer process of the above (2) except that the secondary feature map 301 is used instead of the primary feature map 101. Due to this, the image analysis device generates a reduced secondary feature map 401. The reduced secondary feature map 401 includes (10×10) pixels constituted of 10 pixels aligned along the lateral direction and 10 pixels aligned along the vertical direction. The image analysis device executes same processes on the other secondary feature maps 302 to 306 as well and generates a plurality of reduced secondary feature maps 402 to 406 corresponding to the plurality of secondary feature maps 302 to 306.

(5) The image analysis device uses the plurality of reduced secondary feature maps 401 to 406 as generated and outputs a result of the image analysis in an output layer. In this embodiment, an output layer process is executed through two convolutional layer processes and two pooling layer processes, however, in a variant, the output layer process may be executed after having further executed convolutional layer and pooling layer processes on the reduced secondary feature maps 401 to 406. The result of the image analysis may be a number of each of the plural types of cell objects included in the target image data, for example, or may be a density per unit area of each cell. Further, the image analysis device is configured capable of executing learning based on the outputted result to modify the pattern data 42, for example.

As above, in the conventional image analysis, the image analysis is executed by using the reduced image data in which the target image data is reduced, for purpose of speeding up the image analysis. However, as shown in FIG. 2, a contour and the like of the object may become unclear in a reduced image 502 as compared to a target image 500, by which analysis accuracy may be degraded. To solve this problem, the present embodiment executes the following processes in addition to the conventional image analysis.

Figure 4:
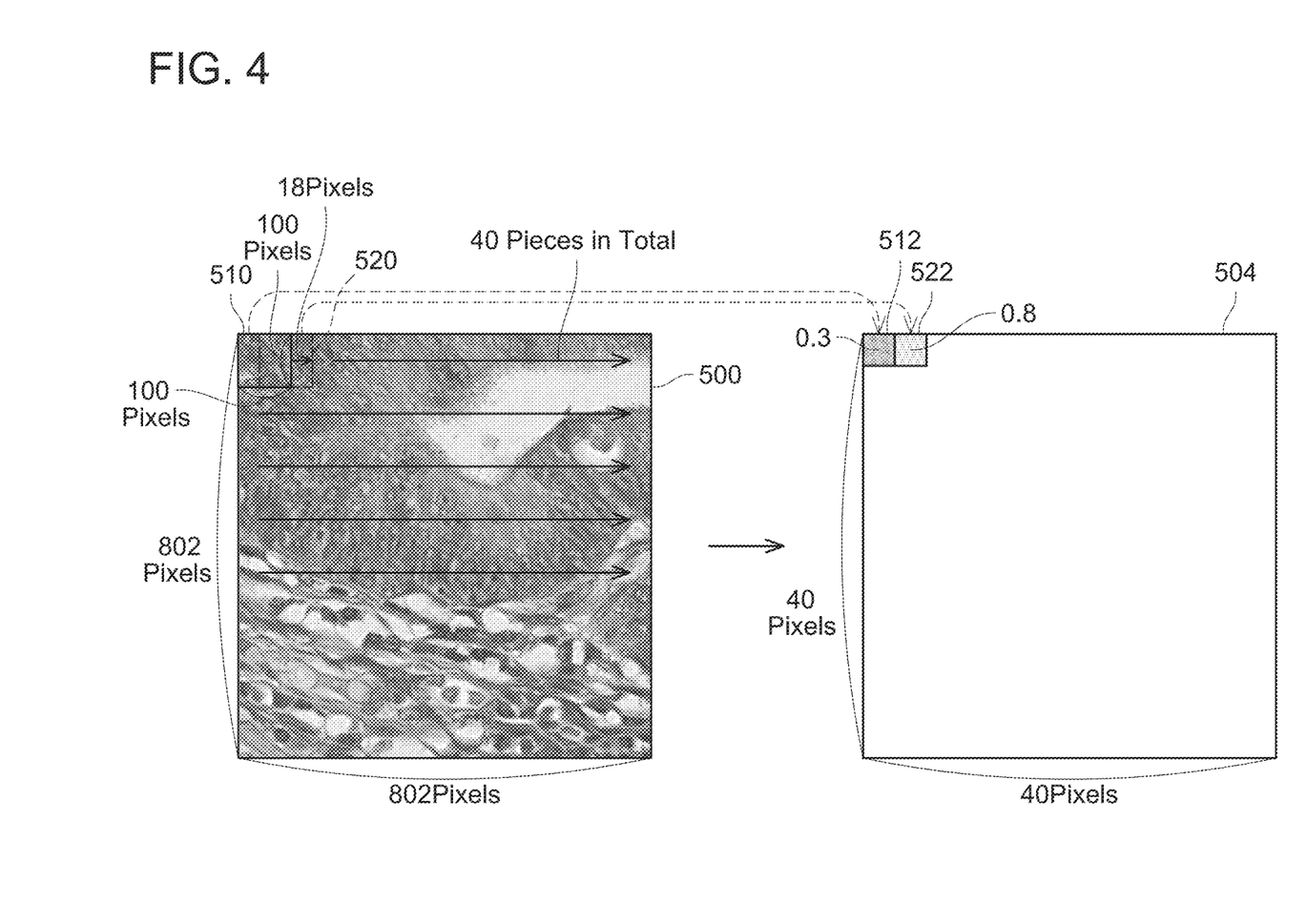
FIG. 4 shows an explanatory diagram for explaining a generation process of probability data.
Figure 5:
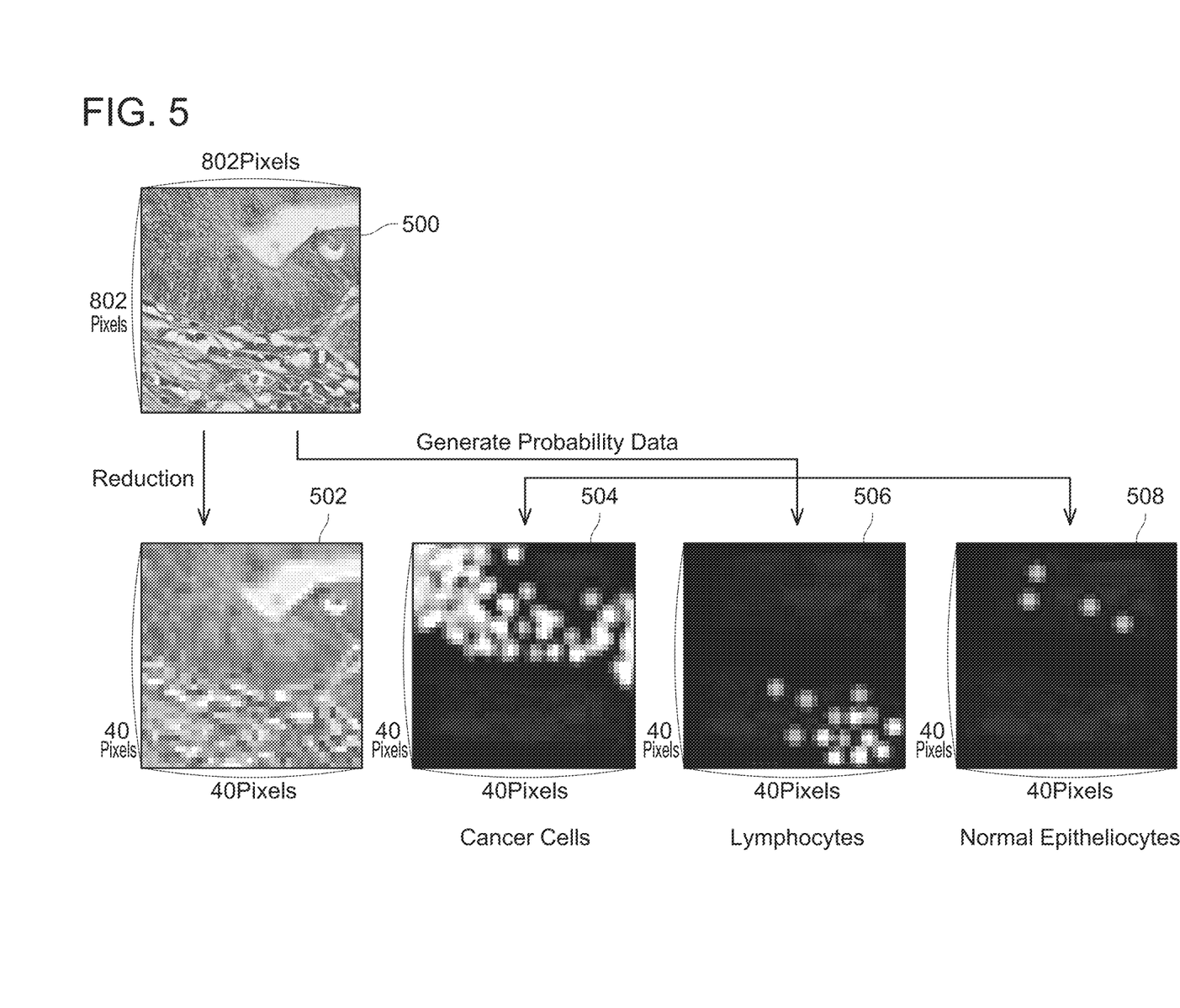
FIG. 5 shows an example of probability data of each cell.
Figure 6A:
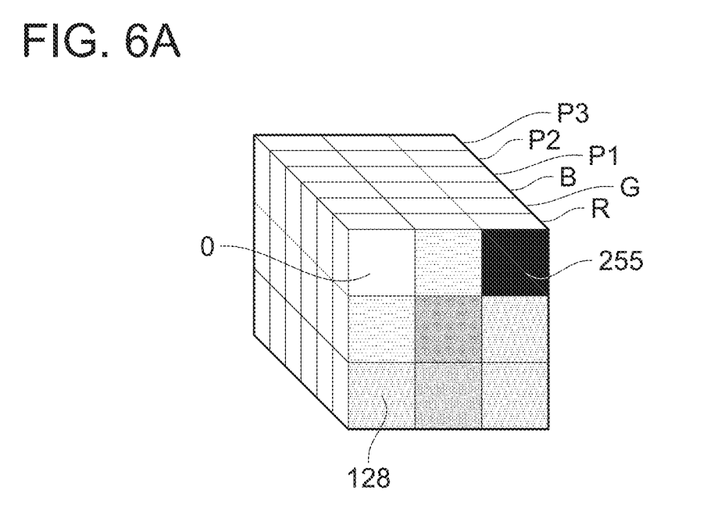
FIGS. 6A and 6B show an explanatory diagram for explaining image analysis of the present embodiment.
Figure 6B:
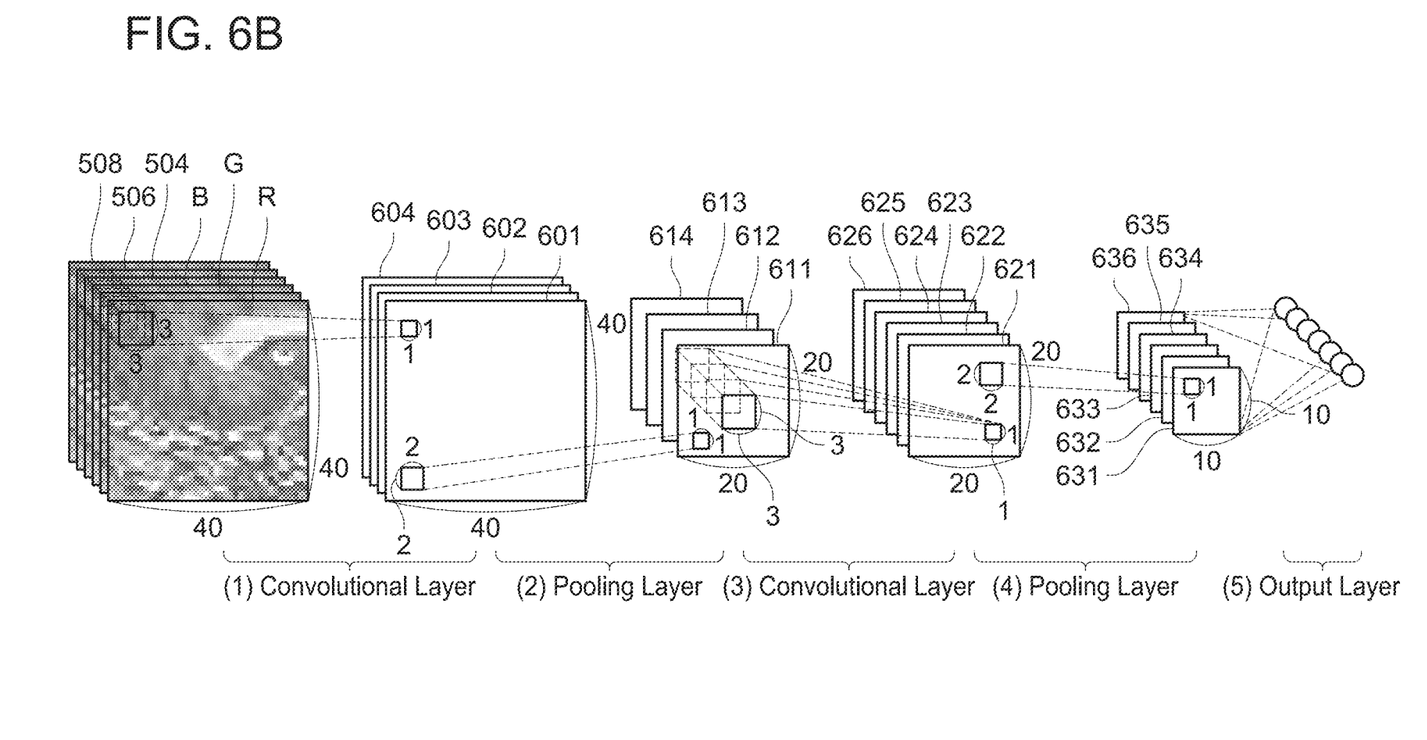

(Image Analysis of Present Embodiment: FIGS. 4 to 6)

Next, contents of the image analysis which the CPU 32 of the image analysis device 10 of the present embodiment executes according to the analysis program 38 will be described with reference to FIGS. 4 to 6. Firstly, a generation process in which the CPU 32 generates probability data will be described with reference to FIG. 4. The CPU 32 obtains target image data inputted to the input unit 16. Then, the CPU 32 generates the probability data as follows.

(Generation Process of Probability Data: FIG. 4)

Firstly, the CPU 32 specifies a first partial image 510 from the target image 500 represented by the target image data. The first partial image 510 includes (100×100) pixels constituted of 100 pixels aligned along the lateral direction and 100 pixels aligned along the vertical direction. Then, the CPU 32 shifts 18 pixels rightward from the first partial image 510 and specifies a second partial image 520. The second partial image 520 also includes (100×100) pixels constituted of 100 pixels aligned along the lateral direction and 100 pixels aligned along the vertical direction. Similarly, the CPU 32 scans the target image 500 rightward and sequentially specifies 40 partial images aligned along the lateral direction. When a rightmost partial image is specified, the CPU 32 shifts 18 pixels downward from the first partial image 510 and specifies a next partial image from the target image 500. Then, similar to the above, the CPU 32 scans rightward from this partial image and sequentially specifies 40 partial images aligned along the lateral direction. By repeating the above, the CPU 32 sequentially specifies (40×40) partial images constituted of 40 partial images aligned along the lateral direction and 40 partial images aligned along the vertical direction. Here, a number of the partial images aligned along the lateral direction (that is, 40) and a number of the partial images aligned along the vertical direction (that is, 40) respectively match the number of pixels in the lateral direction and the number of pixels in the vertical direction in the reduced image data (see 502 in FIG. 2 as above). Further, in a variant, these numbers may be any numbers other than "40" so long as the numbers of the partial images and the numbers of the pixels in the reduced image data match.

Next, the CPU 32 uses the object data 44 representing the cancer cell and calculates a probability that each of the specified partial images includes the cancer cell. This probability is represented by a value in a range from "0" to "1", and becomes a value closer to "1" with a higher probability that the partial image includes the cancer cell. In a variant, the probability may be represented by a value in a range from "0%" to "100%". Further, in another variant, it may become a value closer to "0" with the higher probability that the partial image includes the cancer cell.

For example, the CPU 32 calculates "0.3" as the probability that the first partial image 510 includes the cancer cell, and describes the probability "0.3" as the value of a pixel 512 corresponding to the first partial image 510. Similarly, the CPU 32 calculates "0.8" as the probability that the second partial image 520 includes the cancer cell, and describes the probability "0.8" as the value of a pixel 522 corresponding to the second partial image 520. The CPU 32 calculates probabilities for the other partial images similarly, and generates probability data 504 in which the respectively calculated probabilities are described. The probability data 504 includes (40×40) pixels constituted of 40 pixels aligned along the lateral direction and 40 pixels aligned along the vertical direction. In the probability data 504 of FIG. 4, values of the respective probabilities are represented by darkness of pixels, and a pixel is whiter with a higher probability (that is, being closer to "1"). FIG. 5 shows an example of the probability data 504 corresponding to the cancer cell. In FIG. 5 as well, pixels are whiter with the higher probability. The generation process as above is not limited to the CNN, but may be executed according to a support vector machine or a decision tree.

The CPU 32 further uses the object data 44 representing the lymphocyte and generates probability data 506 (see FIG. 5) similar to the above. Further, the CPU 32 further uses object data (not shown) representing the normal epitheliocyte and generates probability data 508 similar to the above.

(Image Analysis of Present Embodiment: FIG. 6)

Continuingly, the contents of the image analysis of the present embodiment will be described with reference to FIG. 6. The image analysis of the present embodiment differs from the conventional image processing in (1) of FIG. 3 in regard to a process in the first convolutional layer. Specifically, the CPU 32 uses the reduced image data as the three pieces of channel data corresponding to the three channels of RGB as has been the case with the conventional image processing, however, the CPU 32 further executes the convolutional layer process using the probability data 504 as one piece of channel data corresponding to one channel. The CPU 32 further executes the convolutional layer process using the probability data 506 as one piece of channel data corresponding to one channel, and also the probability data 508 as one piece of channel data corresponding to one channel.

Specifically, the CPU 32 firstly reduces the target image data to generate the reduced image data similar to the conventional image processing, and executes respective processes of (1) to (5) of FIG. 6. (1) The CPU 32 executes the convolutional layer process by using not only the generated reduced image data but also the three pieces of probability data 504, 506, 508 as three pieces of channel data. Six-layer pattern data included in the pattern data 42 is used in the convolutional layer hereof. FIG. 6(A) shows an example of the six-layer pattern data. The six-layer pattern data includes one layer of data corresponding to the R values, one layer of data corresponding to the G values, one layer of data corresponding to the B values, one layer of data corresponding to a probability P1 that the cancer cell is present, one layer of data corresponding to a probability P2 that the lymphocyte is present, and one layer of data corresponding to a probability P3 that the normal epitheliocyte is present. Each of the six layers of data includes (3×3) pixels constituted of 3 pixels aligned along the lateral direction and 3 pixels aligned along the vertical direction. That is, the six-layer pattern data is constituted of (3×3×6) pixels.

The CPU 32 specifies (3×3) pixels included in the reduced image data as a target pixel group and compares (3×3) R values included in this target pixel group with (3×3) R values included in the one layer corresponding to the R values in the three-layer pattern data. Similarly, the CPU 32 executes comparisons for the G values and the B values as well. Further, the CPU 32 specifies (3×3) pixels included in the probability data 504 corresponding to the cancer cell as a target pixel group and compares (3×3) values included in this target pixel group with (3×3) values included in the one layer of data corresponding to the probability P1 in the six-layer pattern data. Similarly, the CPU 32 executes comparisons for the probability data 506, 508 corresponding to the lymphocyte and the normal epitheliocyte as well. Then, the CPU 32 uses the respective comparison results to calculate match rates between the target pixel groups and the six-layer pattern data. The CPU 32 generates a primary feature map 601 in which respectively specified match rates are described by sequentially specifying the target pixel groups from the reduced image data and the probability data 504, 506, 508 and sequentially specifying the match rates thereof. The primary feature map 601 includes (40×40) pixels constituted of 40 pixels aligned along the lateral direction and 40 pixels aligned along the vertical direction, and each pixel indicates the match rate. Since the pattern data 42 includes a plurality of pieces of six-layer pattern data, the CPU 32 executes the convolutional layer process for each of the plurality of pieces of six-layer pattern data and generates a plurality of primary feature maps 601 to 604 corresponding to the plurality of pieces of six-layer pattern data.

The processes of (2) to (5) are same as those of (2) to (5) of FIG. 3 except that the plurality of primary feature maps 601 to 604 is used. That is, (2) the pooling layer process is executed for the plurality of primary feature maps 601 to 604 by which a plurality of reduced primary feature maps 611 to 614 is generated, and (3) the convolutional layer process is executed for the plurality of reduced primary feature maps 611 to 614 by which a plurality of secondary feature maps 621 to 626 is generated. Further, (4) the pooling layer process is executed for the plurality of secondary feature maps 621 to 626 by which a plurality of reduced secondary feature maps 631 to 636 is generated, and (5) a result of the image analysis is outputted.

(Effects of Present Embodiment)

For example, in the conventional image analysis, an analysis result with high analysis accuracy may be obtained by employing a configuration that uses target image data as three pieces of channel data corresponding to three channels without reducing the target image data. However, as aforementioned, the target image data includes (802×802) pixels, and as such, a long period of time is required and a high memory volume is consumed in the convolutional layer process in (1) of FIG. 3(C). Further, since each primary feature map generated by the convolutional layer process also includes (802×802) pixels, each reduced primary feature map generated in the pooling layer in (2) of FIG. 3(C) also includes (401×401) pixels, by which a long period of time is required and a high memory volume is consumed also in the convolutional layer and the pooling layer process which take place thereafter.

Thus, in the present embodiment, the image analysis device 10 uses the reduced image data as the three pieces of channel data corresponding to the three channels in executing the image analysis according to the CNN, so that the image analysis can be executed promptly. Here, in order to improve the analysis accuracy, the image analysis device 10 uses the probability data 504 as the one piece of channel data corresponding to the one channel in addition to the reduced image data as the three pieces of channel data corresponding to the three channels. Due to this, the image analysis device 10 can improve analysis accuracy related to the image including the cancer cell in the image analysis using the reduced image data. Further, in the present embediment, the image analysis device 10 further uses the probability data 506 as the one piece of channel data corresponding to the one channel and also the probability data 508 as the one piece of channel data corresponding to the one channel. By doing so, the image analysis device 10 can further improve both analysis accuracy related to the image including the lymphocyte and analysis accuracy related to the image including the normal epitheliocyte in the image analysis using the reduced image data.

For example, Japanese Patent Application Publication Nos. 2004-286666 and 2010-281636 describe techniques related to image analysis. The art disclosed in the present embodiment (which the inventor calls the "component channel CNN (cc-CNN)") completely differs from such conventional techniques, and executes the CNN using the probability data 504 to 508 corresponding to the cancer cell and the like as the channel data. Due to this, prompting of the image analysis, suppression of memory consumption, and high analysis accuracy can be realized.

(Corresponding Relationship)

The cancer cell and the lymphocyte are respectively an example of a "first object" and a "second object". The lateral direction and the vertical direction are respectively an example of a "first direction" and a "second direction". The (802×802) pixels in the target image data is an example of "(M×N) pixels" and the three channels of RGB are an example of "K channels". The (40×40) partial images are an example of "(m×n) partial images". The (40×40) pixels in the probability data are an example of "(m×n) pixels". The probability data 504 and the probability data 506 are respectively an example of "first probability data" and "second probability data".

An embodiment has been described in detail, however, these are mere exemplary indications and thus do not limit the scope of the claims. The art described in the claims include modifications and variations of the specific examples presented above.

(Variant 1) Not being limited to the image analysis on images including cells, the image analysis device 10 may execute the image analysis on images including other objects (such as a human or a tree). In this case, the image analysis device 10 stores a piece of object data representing a human and a piece of object data representing a tree as the pieces of object data 44. For example, in a case of obtaining target image data representing an image of a scenery including a human and a tree as the target image, the image analysis device 10 generates a piece of probability data representing a probability that a human is present and a piece of probability data representing a probability that a tree is present based on the target image data. Then, the image analysis device 10 executes the CNN using reduced image data obtained by reducing the target image data and the plurality of pieces of probability data that were respectively generated, by which the image analysis related to the human and the tree can be executed promptly and highly accurately. That is, in this variant, any one of the human and the tree is an example of the "first object" and the "first object" may not be a predetermined cell.

(Variant 2) In the above embodiment, the respective pixels constituting the target image data include the three values corresponding to the three channels of RGB. Instead of this, the respective pixels constituting the target image data may include only one value corresponding to one channel such as a luminance value. In this case, the respective pixels constituting the reduced image data also include only one value corresponding to the one channel. Further, in (1) of FIG. 6(C), instead of the six-layer pattern data, four-layer pattern data including one layer of data corresponding to the luminance value, the one layer of data corresponding to the probability P1 that the cancer cell is present, the one layer of data corresponding to the probability P2 that the lymphocyte is present, and the one layer of data corresponding to the probability P3 that the normal epitheliocyte is present is used. That is, in the present variant, the "K" is 1. In another variant, the "K" may be 2, or may be 4 or more.

(Variant 3) In a variant, the probability data 506, 508 may not be used. That is, at least one probability data may be used. In the present variant, a "second generating unit" may be omitted. Further, in another variant, additional piece of probability data may be generated and the convolutional layer process in (1) of FIG. 6(C) may be executed with this additional piece of probability data being further be used as one piece of channel data. That is, a number of the probability data may be 3 or more.

(Variant 4) In the respective embodiments as above, the processes of FIGS. 4 and 6 are realized by software (that is, the analysis program 38), however, at least one of these processes may be realized by hardware such as a logic circuit.

Moreover, technical features described in the description and the drawings may technically be useful alone or in various combinations, and are not limited to the combinations as originally claimed. Further, the art described in the description and the drawings may concurrently achieve a plurality of aims, and technical significance thereof resides in achieving any one of such aims.

REFERENCE SIGNS LIST

10: image analysis device, 12: operation unit, 14: display, 16: input unit, 30: controller, 34: memory, 36: OS program, 38: analysis program, 40: analysis data, 42: pattern data, 44: object data, 101, 102, 103, 104, 601, 602, 603, 604: primary feature map, 201, 202, 203, 204, 611, 612, 613, 614: reduced primary feature map, 301, 302, 303, 304, 305, 306, 621, 622, 623, 624, 625, 626: secondary feature map, 401, 402, 403, 404, 405, 406, 631, 632, 633, 634, 635, 636: reduced secondary feature map, 500: target image, 502: reduced image, 510, 520: partial image, 512, 522: pixel, 504, 506, 508: probability data

The invention claimed is:

1. An image analysis device comprising:
a memory configured to store first object data representing a first object;
an obtaining unit configured to obtain target image data representing a target image which is an analysis target, wherein the target image data includes (M×N) pixels constituted of M pixels aligned along a first direction and N pixels aligned along a second direction orthogonal to the first direction, the M being an integer of 3 or greater, and the N being an integer of 3 or greater, and wherein each pixel of the (M×N) pixels indicates K values corresponding to K channels, the K being an integer of 1 or greater;
a specifying unit configured to specify (m×n) partial images sequentially by scanning the target image data, wherein the (m×n) partial images are constituted of m partial images aligned along the first direction and n partial images aligned along the second direction, the m being an integer of 2 or greater and less than the M, and the n being an integer of 2 or greater and less than the N;
a generating unit configured to generate L pieces of additional channel data including first probability data by using the (m×n) partial images and the first object data in the memory, the L being an integer of 1 or greater, wherein the first probability data includes (m×n) pixels constituted of m pixels aligned along the first direction and n pixels aligned along the second direction, and wherein each pixel of the (m×n) pixels included in the first probability data indicates a value related to a probability that one partial image corresponding to the pixel includes the first object;
a reducing unit configured to reduce the target image data so as to generate reduced image data, wherein the reduced image data includes (m×n) pixels constituted of m pixels aligned along the first direction and n pixels aligned along the second direction, wherein (K+L) pieces of channel data corresponding to (K+L) channels are generated by using the reduced image data as K pieces of channel data corresponding to the K channels and using the L pieces of additional channel data as L pieces of channel data corresponding to L additional channels;
an analysis unit configured to execute an image analysis according to a convolutional neural network by using the (K+L) pieces of channel data, wherein
the image analysis includes executing a convolutional layer process by using the (K+L) pieces of channel data corresponding to the (K+L) channels and (K+L) pieces of pattern data prepared in advance and corresponding to the (K+L) channels,
each piece of the (K+L) pieces of pattern data includes (m'×n') pixels constituted of m' pixels aligned along the first direction and n' pixels aligned along the second direction, the m' being an integer less than the m, and the n' being an integer less than the n, and
the convolutional layer process includes a process of specifying, for each of the (K+L) channels, a match rate between a target pixel group in a piece of channel data corresponding to the channel and a piece of the pattern data corresponding to the channel; and
an output unit configured to output a result of the image analysis.

2. The image analysis device according to claim 1, wherein the K channels are three channels of RGB.

3. The image analysis device according to claim 1, wherein
the memory is further configured to store second object data representing a second object different from the first object,
the generating unit is further configured to generate the L pieces of additional channel data further including second probability data by using the (m×n) partial images and the second object data in the memory,
wherein the second probability data includes (m×n) pixels constituted of m pixels aligned along the first direction and n pixels aligned along the second direction, and each pixel of the (m×n) pixels included in the second probability data indicates a value related to a probability that one partial image corresponding to the pixel includes the second object, and
the (K+L) pieces of channel data are generated by using the L pieces of additional channel data including the first probability data and the second probability data.

4. The image analysis device according to claim 1, wherein the first object is a predetermined cell.

5. A non-transitory computer readable medium comprising instructions for realizing an image analysis device, wherein the instructions, when executed by a computer processing unit, cause the computer processing unit to:
obtain target image data representing a target image which is an analysis target, wherein the target image data comprises (M×N) pixels constituted of M pixels aligned along a first direction and N pixels aligned along a second direction orthogonal to the first direction, the M being an integer of 3 or greater, and the N being an integer of 3 or greater, and wherein each pixel of the (M×N) pixels indicates K values corresponding to K channels, the K being an integer of 1 or greater;
specify (m×n) partial images sequentially by scanning the target image data, wherein the (m×n) partial images are constituted of m partial images aligned along the first direction and n partial images aligned along the second direction, the m being an integer of 2 or greater and less than the M, and the n being an integer of 2 or greater and less than the N;
generate L pieces of additional channel data comprising first probability data by using the (m×n) partial images and first object data representing a first object, the L being an integer of 1 or greater, wherein the first probability data comprises (m×n) pixels constituted of m pixels aligned along the first direction and n pixels aligned along the second direction, and each pixel of the (m×n) pixels in the first probability data indicates a value related to a probability that one partial image corresponding to the pixel comprises the first object;
reduce the target image data so as to generate reduced image data, wherein the reduced image data comprises (m×n) pixels constituted of m pixels aligned along the first direction and n pixels aligned along the second direction, wherein (K+L) pieces of channel data corresponding to (K+L) channels are generated by using the reduced image data as K pieces of channel data corresponding to the K channels and using the L pieces of additional channel data as L pieces of channel data corresponding to L additional channels;

execute an image analysis according to a convolutional neural network by using the (K+L) pieces of channel data, wherein the image analysis comprises executing a convolutional layer process by using the (K+L) pieces of channel data corresponding to the (K+L) channels and (K+L) pieces of pattern data prepared in advance and corresponding to the (K+L) channels, each piece of the (K+L) pieces of pattern data comprises (m'×n') pixels constituted of m' pixels aligned along the first direction and n' pixels aligned along the second direction, the m' being an integer less than the m, and the n' being an integer less than the n, and the convolutional layer process comprises a process of specifying, for each of the (K+L) channels, a match rate between a target pixel group in a piece of channel data corresponding to the channel and a piece of the pattern data corresponding to the channel; and output a result of the image analysis.

6. A method of analyzing an image, the method comprising:

an obtaining step of obtaining target image data representing a target image which is an analysis target, wherein the target image data includes (M×N) pixels constituted of M pixels aligned along a first direction and N pixels aligned along a second direction orthogonal to the first direction, the M being an integer of 3 or greater, the N being an integer of 3 or greater, and wherein each pixel of the (M×N) pixels indicates K values corresponding to K channels, the K being an integer of 1 or greater;

a specifying step of specifying (m×n) partial images sequentially by scanning the target image data, wherein the (m×n) partial images are constituted of m partial images aligned along the first direction and n partial images aligned along the second direction, the m being an integer of 2 or greater and less than the M, and the n being an integer of 2 or greater and less than the N;

a generating step of generating L pieces of additional channel data including first probability data by using the (m×n) partial images and first object data representing a first object, the L being an integer of 1 or greater, wherein the first probability data includes (m×n) pixels constituted of m pixels aligned along the first direction and n pixels aligned along the second direction, and each pixel of the (m×n) pixels included in the first probability data indicates a value related to a probability that one partial image corresponding to the pixel includes the first object;

a reducing step of reducing the target image data so as to generate reduced image data, wherein the reduced image data includes (m×n) pixels constituted of m pixels aligned along the first direction and n pixels aligned along the second direction, wherein (K+L) pieces of channel data corresponding to (K+L) channels are generated by using the reduced image data as K pieces of channel data corresponding to the K channels and using the L pieces of additional channel data as L pieces of channel data corresponding to L additional channels;

an analysis step of executing an image analysis according to a convolutional neural network by using the (K+L) pieces of channel data, wherein the image analysis includes executing a convolutional layer process by using the (K+L) pieces of channel data corresponding to the (K+L) channels and (K+L) pieces of pattern data prepared in advance and corresponding to the (K+L) channels, each piece of the (K+L) pieces of pattern data includes (m'×n') pixels constituted of m' pixels aligned along the first direction and n' pixels aligned along the second direction, the m' being an integer less than the m, and the n' being an integer less than the n, and the convolutional layer process includes a process of specifying, for each of the (K+L) channels, a match rate between a target pixel group in a piece of channel data corresponding to the channel and a piece of the pattern data corresponding to the channel; and an output step of outputting a result of the image analysis.

* * * * *